United States Patent [19]

Hausberg et al.

[11] Patent Number: 4,914,114

[45] Date of Patent: Apr. 3, 1990

[54] 3-[4-(4-PHENYL-1,2,3,6-TETRAHYDRO-1-PYRIDYL)BUTYL]-5-HYDROXY-INDOLE METHANESULFONATE HAVING SEDATING AND ANTI-PARKINSONISM PROPERTIES

[75] Inventors: Hans-Heinrich Hausberg, Ober-Ramstadt; Henning Böttcher, Darmstadt; Christoph Seyfried, Seeheim-Jugenheim; Rolf Bergmann, Reichelsheim, all of Fed. Rep. of Germany

[73] Assignee: Merck Patent Gesellschaft Mit Breschrankter Haftung, Darmstadt, Fed. Rep. of Germany

[21] Appl. No.: 213,571

[22] PCT Filed: Sep. 12, 1987

[86] PCT No.: PCT/EP87/00518

§ 371 Date: May 16, 1988

§ 102(e) Date: May 16, 1988

[87] PCT Pub. No.: WO88/01998

PCT Pub. Date: Mar. 24, 1988

Related U.S. Application Data

[60] Division of Ser. No. 907,909, Sep. 16, 1986, Pat. No. 4,711,983, which is a continuation-in-part of Ser. No. 738,329, May 28, 1985, abandoned.

[51] Int. Cl.$^4$ ................ C07D 401/06; A61K 31/435
[52] U.S. Cl. ..................................... 514/339; 546/273
[58] Field of Search ......................... 546/273; 514/339

[56] References Cited

U.S. PATENT DOCUMENTS

| 4,131,680 | 12/1978 | Archibald et al. | 514/323 |
| 4,238,215 | 3/1966 | Zenitz | 546/201 |
| 4,251,538 | 2/1981 | Hausberg et al. | 514/323 |

Primary Examiner—Alan L. Rotman
Attorney, Agent, or Firm—Millen, White & Zelano

[57] ABSTRACT

3-[4-(4-phenyl-1,2,3,6-tetrahydro-1-pyridyl)butyl]-5-hydroxy-indole methanesulfonate can be used in the therapy of Parkinsonism and is particularly readily soluble.

5 Claims, No Drawings

3-[4-(4-PHENYL-1,2,3,6-TETRAHYDRO-1-PYRIDYL)BUTYL]-5-HYDROXY-INDOLE METHANESULFONATE HAVING SEDATING AND ANTI-PARKINSONISM PROPERTIES

CROSS-REFERENCE TO RELATED APPLICATIONS

This application is the U.S. National Phase of PCT/EP87/00518, filed Sept. 12, 1987, and is a divisional of U.S. Ser. No. 907,909, filed Sept. 16, 1986 (now U.S. Pat. No. 4,711,983), which is a continuation-in-part of U.S. Ser. No. 738,329, filed May 28, 1985.

The invention relates to the new compound 3-[4-(4-phenyl-1,2,3,6-tetrahydro-1-pyridyl)-butyl]-5-hydroxyindole methanesulfonate (I).

The underlying base (II) and the corresponding hydrochloride (III) are described in DE-OS 2,910,367.

It has been found that I has considerably more favourable pharmacokinetic properties than III. Thus, for example, 100 mg/kg of I administered orally to Cynomolgus monkeys already lead to a sedating reaction, whilst this effect can be achieved with III only with doses above 500 mg/kg. I also has a considerably better solubility in water (0.921 g in 100 ml) than III (0.035 g in 100 ml).

The invention accordingly relates to the new compound I and a process for its preparation, which comprises reacting the base II with methanesulfonic acid.

This reaction is advantageously carried out in an inert solvent, for example methanol or ethanol, at temperatures between 0° and 80°, preferably between 15° and 30°. Stoichiometric amounts of the starting substances are preferably used.

The compound I can be used to prepare pharmaceutical formulations, in particular by a non-chemical route. For this, they can be brought into a suitable dosage form together with at least one solid, liquid or semi-liquid excipient or auxiliary and if appropriate in combination with one or more other active compound(s).

The invention furthermore relates to pharmaceutical formulations contining the compound I. These formulations can be used as medicaments in human or veterinary medicine. Possible excipients are organic or inorganic substances which are suitable for enteral (for example oral) or parenteral administration or topical application and do not react with the new compound, for example water, vegetable oils, benzyl alcohols, polyethylene glycols, gelatine, carbohydrates, such as lactose or starch, magnesium stearate, talc and vaseline. Tablets, coated tablets, capsules, syrups, elixirs, drops or suppositories are used, in particular, for enteral administration, solutions, preferably oily or aqueous solutions, and furthermore suspensions, emulsions or implants, are used for parenteral administration and ointments, creams or powders are used for topical application. The new compound can also be lyophilized and the resulting lyophilisates can be used, for example, to produce injection preparations. The formulations mentioned can be sterilized and/or contain auxiliaries, such as lubricants, preservatives, stabilizers and/or wetting agents, emulsifiers, salts for influencing the osmotic pressure, buffer substances, dyestuffs, flavouring substances and/or aroma substances. If desired, they can also contain one or more other active compounds, for example one or more vitamins.

The compound I can be administered to humans or animals, in particular mammals, such as monkeys, dogs, cats, rats or mice, and can be used in the therapeutic treatment of the human or animal body and in combating diseases, in particular in the therapy of Parkinsonism, extrapyramidal disturbances in neuroleptic therapy, depression and/or psychoses and side effects in the treatment of hypertension (for example with α-methyldopa). The compound I can also be used in endocrinology and gynaecology, for example for the therapy of acromegaly, hypogonadism, secondary amenorrhoea, premenstrual syndrome, undesirable puerperal lactation and generally as a prolactin inhibitor, and furthermore for the therapy of cerebral disturbances (for example migraine), in particular in geriatrics in the same way as certain ergot alkaloids, and also for reducing blood pressure.

The compound I is as a rule thereby administered analogously to known commercially available preparations (for example bromocriptine and dihydroergocornine), preferably in dosages of between about 0.05 and 5 mg, in particular between 0.2 and 2 mg per dosage unit. The daily dosage is preferably between about 0.001 and 0.1 mg/kg of body weight. However, the specific dose for each particular patient depends on the most diverse factors, for example on the age, body weight, general state of health, sex, diet, administration time and method, rate of excretion, drug combination and the severity of the particular disease to which the therapy applies. Oral administration is preferred.

Preparation Example

A solution of 7 g of methanesulfonic acid in 40 ml of ethanol is added to a suspension of 23 g of 3-[4-(4-phenyl-1,2,3,6-tetrahydropyridyl)-butyl]-5-hydroxyindole (II) in 340 ml of ethanol at 15° C., the mixture is warmed briefly to 30° C. and cooled to 15° C. and the resulting 3-[4-(4-phenyl-1,2,3,6-tetrahydro-1-pyridyl)-butyl]-5-hydroxyindole methanesulfonate (I) is filtered off. Melting point 176° C.

The following examples relate to pharmaceutical formulations containing the compound I:

EXAMPLE A

Tablets

A mixture of 1 kg of I, 4 kg of lactose, 1.2 kg of potato starch, 0.2 kg of talc and 0.1 kg of magnesium stearate is pressed into tablets in the customary manner such that each tablet contains 1 mg of active compound.

EXAMPLE B

Coated Tablets

Tablets are pressed analogously to Example A and are then coated in the customary manner with a coating of sucrose, potato starch, talc, tragacanth and dyestuff.

EXAMPLE C

Capsules

Hard gelatine capsules are filled with 10 kg of I in the customary manner such that each capsule contains 1 mg of active compound.

EXAMPLE D

Ampoules

A solution of 1 kg of I in 30 l of doubly-distilled water is subjected to sterile filtration and ampoules are filled with the solution, lyophilized under sterile conditions and subjected to sterile sealing. Each ampoule contains 0.5 mg of active compound.

We claim:

1. 3-[4-(4-Phenyl-1,2,3,6-tetrahydro-1-pyridyl)-butyl]-5-hydroxy-indole methanesulfonate (I).

2. A pharmaceutical composition comprising the compound of claim 1 and a pharmaceutically acceptable carrier.

3. A pharmaceutical composition of claim 2 containing 0.2 to 2 mg of said compound.

4. A method of achieving a sedating effect comprising administering the compound of claim 1.

5. A method of treating Parkinsonism comprising administering a compound of claim 1.

* * * * *

UNITED STATES PATENT AND TRADEMARK OFFICE
CERTIFICATE OF CORRECTION

PATENT NO. : 4,914,114

DATED : April 3, 1990

INVENTOR(S) : HANS-HEINRICH HAUSBERG ET AL

It is certified that error appears in the above-identified patent and that said Letters Patent is hereby corrected as shown below:

Column 3, claim 2, line 9:

reads "A pharmaceutical composition comprising the"

should read -- A pharmaceutical composition comprising an effective amount of the --

Column 4, claim 3, lines 3 and 4:

reads "A pharmaceutical composition of claim 2 containing 0.2 to 2 mg of said compound.

should read -- A pharmaceutical composition of claim 2, wherein the range is 0.2 to 2 mg of said compound. --

Column 4, claim 4, line 6:

reads "ing administering the compound of claim 1."

should read -- ing administering to a mammal in need of said treatment, an effective amount of the compound of claim 1. --

UNITED STATES PATENT AND TRADEMARK OFFICE
CERTIFICATE OF CORRECTION

PATENT NO. : 4,914,114

DATED : April 3, 1990

INVENTOR(S) : HANS-HEINRICH HAUSBERG ET AL

It is certified that error appears in the above-identified patent and that said Letters Patent is hereby corrected as shown below:

Column 4, claim 5, ~~line~~ line 8:

reads "administering a compound of claim 1."

should read -- administering to a mammal in need of said treatment, an effective amount of the compound of claim 1. --

Signed and Sealed this

Ninth Day of July, 1991

Attest:

HARRY F. MANBECK, JR.

*Attesting Officer*      *Commissioner of Patents and Trademarks*